United States Patent [19]

Steiner et al.

[11] Patent Number: 5,801,197
[45] Date of Patent: Sep. 1, 1998

[54] ROTAMASE ENZYME ACTIVITY INHIBITORS

[75] Inventors: Joseph P. Steiner, Hampstead; Gregory S. Hamilton, Catonsville, both of Md.

[73] Assignee: GPI NIL Holdings, Inc., Wilmington, Del.

[21] Appl. No.: 645,149

[22] Filed: May 13, 1996

Related U.S. Application Data

[63] Continuation-in-part of Ser. No. 551,026, Oct. 31, 1995, abandoned.

[51] Int. Cl.$^6$ .................... A61K 31/445; A61K 31/40; A61K 31/22; A61K 31/24
[52] U.S. Cl. .................... 514/548; 514/330; 514/423; 514/428; 514/534; 514/538; 514/547; 514/549; 514/551; 514/465; 514/466; 549/441; 560/39; 560/43; 560/170
[58] Field of Search ................... 514/548, 330, 514/473, 478, 534, 538, 547, 549, 551, 465, 466; 549/441; 560/39, 43, 170

[56] References Cited

U.S. PATENT DOCUMENTS

| | | |
|---|---|---|
| 4,310,461 | 1/1982 | Krapcho et al. . |
| 4,374,829 | 2/1983 | Harris et al. . |
| 4,390,695 | 6/1983 | Krapcho et al. . |
| 4,531,964 | 7/1985 | Shimano et al. . |
| 4,574,079 | 3/1986 | Gavras et al. . |
| 4,578,474 | 3/1986 | Krapcho et al. . |
| 4,593,102 | 6/1986 | Shanklin, Jr. . |
| 4,808,573 | 2/1989 | Gold et al. . |
| 4,818,749 | 4/1989 | Gold et al. . |
| 5,147,877 | 9/1992 | Goulet . |
| 5,156,797 | 10/1992 | Armistead et al. . |
| 5,252,579 | 10/1993 | Skotnicki et al. . |
| 5,294,603 | 3/1994 | Rinehart . |
| 5,319,098 | 6/1994 | Burbaum et al. . |
| 5,330,993 | 7/1994 | Armistead et al. . |
| 5,359,138 | 10/1994 | Takeuchi et al. . |
| 5,414,083 | 5/1995 | Hackl et al. . |
| 5,424,454 | 6/1995 | Burbaum et al. . |
| 5,447,915 | 9/1995 | Schreiber et al. . |
| 5,543,423 | 8/1996 | Zelle et al. . |

FOREIGN PATENT DOCUMENTS

| | | |
|---|---|---|
| 12401 | 6/1980 | European Pat. Off. . |
| 48159 | 3/1982 | European Pat. Off. . |
| 50800 | 5/1982 | European Pat. Off. . |
| 73143 | 3/1983 | European Pat. Off. . |
| 88350 | 9/1983 | European Pat. Off. . |
| 196841 | 10/1986 | European Pat. Off. . |
| 260118 | 3/1988 | European Pat. Off. . |
| 333174 | 9/1989 | European Pat. Off. . |
| 352000 | 1/1990 | European Pat. Off. . |
| 378318 | 7/1990 | European Pat. Off. . |
| 405994 | 1/1991 | European Pat. Off. . |
| 419049 | 3/1991 | European Pat. Off. . |
| 468339 | 1/1992 | European Pat. Off. . |
| 572365 | 12/1993 | European Pat. Off. . |
| 652229 | 5/1995 | European Pat. Off. . |
| 3508251 | 9/1986 | Germany . |
| 3931051 | 3/1990 | Germany . |
| 4015255 | 11/1991 | Germany . |
| 04149166 | 5/1992 | Japan . |
| 05178824 | 7/1993 | Japan . |
| 9207782 | 4/1993 | South Africa . |
| 2247456 | 3/1992 | United Kingdom . |
| WO8809789 | 12/1988 | WIPO . |
| WO9012805 | 11/1990 | WIPO . |
| WO9104985 | 4/1991 | WIPO . |
| WO9113088 | 9/1991 | WIPO . |
| WO9200278 | 1/1992 | WIPO . |
| WO9203472 | 3/1992 | WIPO . |
| WO9204370 | 3/1992 | WIPO . |
| WO9216501 | 10/1992 | WIPO . |
| WO9218478 | 10/1992 | WIPO . |
| WO9219593 | 11/1992 | WIPO . |
| WO9219745 | 11/1992 | WIPO . |
| WO9221313 | 12/1992 | WIPO . |
| WO9307269 | 4/1993 | WIPO . |
| WO9313066 | 7/1993 | WIPO . |
| WO9323548 | 11/1993 | WIPO . |
| WO9325546 | 12/1993 | WIPO . |
| WO9405639 | 3/1994 | WIPO . |
| WO9407858 | 4/1994 | WIPO . |
| WO9413629 | 6/1994 | WIPO . |
| WO9512572 | 5/1995 | WIPO . |
| WO9524385 | 9/1995 | WIPO . |
| WO9526337 | 10/1995 | WIPO . |
| WO9535308 | 12/1995 | WIPO . |
| WO9535367 | 12/1995 | WIPO . |
| WO9606097 | 2/1996 | WIPO . |
| WO9615101 | 5/1996 | WIPO . |
| WO9617816 | 6/1996 | WIPO . |
| WO 96/41609 | 12/1996 | WIPO . |

OTHER PUBLICATIONS

Askin, D. et al., "Efficient Degradation of FK–506 to a versatile synthetic intermediate," J. Org. Chem., 1990, 55(20), 5451–4.

Goulet, Mark T., and Boger, Joshua, "Degradative studies on the tricarbonyl containing macrolide rapamycin," Tetrahedron Lett., 1990, 31(34), 4845–8.

Jones, T. et al., "Chemistry of tricarbonyl hemiketals and application of Evans technology to the total synthesis of the immunosuppressant (–)–FK–506," J. Am. Chem. Soc., 1990, 112(8), 2998–3017.

(List continued on next page.)

*Primary Examiner*—Keith MacMillan
*Attorney, Agent, or Firm*—Gary M. Nath; Todd L. Juneau; Nath & Associates

[57] ABSTRACT

This invention relates to the method of using specially formulated neurotrophic pipecolic acid derivative compounds having an affinity for FKBP-type immunophilins as inhibitors of the enzyme activity associated with immunophilin proteins, and particularly inhibitors of peptidyl-prolyl isomerase or rotamase enzyme activity to stimulate or promote neuronal growth or regeneration.

4 Claims, 5 Drawing Sheets

OTHER PUBLICATIONS

Jones, A. et al., "A formal synthesis of FK–506. Exploration of some alternatives to macrolactamization," J. Org. Chem., 1990, 55(9), 2786–97.

Rao, A.V., et al., "Studies directed towards the synthesis of immunosuppressive agent FK–506: construction of the tricarbonyl moiety," Tetrahedron Lett., 1990, 31(10), 1439–42.

Harding, M.W., et al., "A receptor for the immunosuppressant FK506 is a cis–trans peptidyl–prolyl isomerase," Nature Lett., 1989, 341, 758–60.

Finberg, Robert W. et al., "Prevention of HIV–1 Infection and Preservation of CD4 Function by the Binding of CPFs to gp120," Science, 1990, 249, 287–91.

Goodfellow, Val S. et al., "p–Nitrophenyl 3–diazopyruvate and diazopyruvamides, a New Family of Photoactivatable Cross–Linking Bioprobes," Biochemistry, 28(15), 6346–60, 1993.

Wasserman, H.H. et al., "Synthesis of the tricarbonyl region of FK–506 through and amidophosphorane [Erratum to document cited in CA111(7):57366p]," J. Org. Chem., 1989, 54(22), 5406.

Wasserman, H.H. et al., "Synthesis of the tricarbonyl region of FK–506 through an amidosphere," J. Org. Chem., 1989, 54(12), 2785–6.

Askin, D. et al., "Chemistry of FK–506: benzilic acid rearrangement of the tricarbonyl system," Tetrahedron Lett., 1989, 30(6), 671–4.

Coleman, R., and Danishefsky, S., "Degradation and manipulations of the immunosuppressant FK506: preparation of potential synthetic intermediates," Heterocycles, 1989, 28(1), 157–61.

Faelth, Lars et al., "Interactions between C=S groups in 1,2–and 1,3–bis(thiocarbonyl) Compounds: A Study by Spectroscopy, X–Ray Crystallography, and CNDO/S Calculations," THEOCHEM, 1989, 55, 239–59.

Boulmedais, Ali et al., "Stererochemistry of Electrochemical Reduction of Optically Active α–ketoamides. II. Electroreduction of benzoylformamides derived from S–(–)–proline," Bull. Soc. Chim. Fr., 1989, (2), 185–91. (French).

Soai, Kenso et al., "Asymmetric Allylation of α–keto amides Derived from (S)–proline esters," Pept. Chem., 1986, 24, 327–330.

Munegumi, Toratane et al., "Asymmetric Catalytic Hydrogenations of N–pyruvoyl–(S)–proline esters," Bull. Chem. Soc. Jpn., 1987, 60(1), 243–53.

Egbertson, M. and Danishefsky, S., "A synthetic route to the tricarbonyl region of FK–506," J. Org. Chem., 1989, 54(1), 11–12.

Williams, D.R. and Benbow, J.W., "Synthesis of the α,β diketo amide segment of the novel immunosuppressive FK506," J. Org. Chem., 1988, 53(191), 4643–4.

Kocienski, P. et al., "A synthesis of the C(1)–C(15) segment of tsukubaenolide (FK506)," Tetrahedron Lett., 1988, 29(35), 4481–4.

Tanaka, H. et al., "Structure of FK506, a novel imunosuppressant isolated from Streptomyces," J. Am. Chem. Soc., 1987, 109(16), 5031–3.

Soai, Kenso and Ishizaki, Miyuki, "Asymmetric Synthesis of Functionalized tertiary alcohols by diastereoselective allylation of chiral α–keto amides derived from (S)–proline esters: control of stereochemistry based on saturated coordination of Lewis acid," J. Org. Chem., 1986, 57(17) 3290–5. (English).

Soai, Kenso et al., "Asymmetric synthesis of both eaniomers of α–hydroxy acids by the diastereoselective reduction of chiral α–keto amides with complex metal hydrides in the presence of a metal salt," Chem. Lett., 1986, 11, 1897–900.

Soai, Kenso and Hasegawa, Hitoshi, "Diasteroselective reduction of chiral α–ketoamides derived from (S)–proline esters with sodium borohydride. Preparation of optically active α–hydroxy acids," J. Chem. Soc., 1985, 1(4), 769–72.

Soai, Kenso and Ishizaki, Miyuki, "Diastereoselective asymmetric allylation of chiral α–keto amides with allyltrimethylsilane. Preparation of protected homoallylic alcohols," J. Chem. Soc., 1984, 15, 1016–1017.

Soai, Kenso et al., "Sodium borohydride as diastereoselective reducing agent of chiral α–keto amides," Pept. Chem., 1982, 20, 81–4.

Bender, D., et al., "Periodate oxidation of α–keto γ–lactams. Enol oxidation and β–lactam formation. Mechanism of periodate hydroxylation reactions," J. Org. Chem., 1978, 43(17), 3354–62.

Colombo, L. et al., "Enantioselective synthesis of secondary alcohols in the presence of chiral ligands," Tetrahedron, 1982, 38(17), 2725–7.

Soai, Kenso et al., "Unusual effect of q mixed solvent on the asymmetric reduction of chiral α–keto amides with sodium borohydride," J. Chem. Soc., 1982, 21, 1282–3.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Cushman, D.W. et al., "Design of potent competitive inhibitors of angiotensin–converting enzyme. Carboxyalkanoyl and mercaptoalkanoyl amino acids," Biochemistry, 1977, 16(25), 5484–91.

Steglich, Wolfgang and Hinze, Sabine, "A rational synthesis of N–trifluroaceytylamino acids," Synthesis, 1976, 8, 399–401. (German).

Bycroft, Barrie W., and Lee, Grahame R., "Efficient asymmetric synthesis of .alpha.–amino from .alpha.–keto acids and ammonia with conservation of the chiral reagent," J. Chem. Soc., 1975, 24, 988–9.

Marshall, J.A. et al., Convenient synthesis of dioxopiperazines via aminolysis of .alpha.–(pyruvylamino) esters, Synth. Commun., 1975, 5(3), 237–44.

Haeusler, Johannes and Schmidt, Ulrich, "Amino acids and peptides. IX. Pyruvoyl amino acids," Chem. Ber., 1974, 107(1), 145–51. (German).

Hearn, Walter R., and Worthington, Robert E., "L–Proline–N–oxalic anhydride," J. Org. Chem., 1967, 32(12), 4072–4.

Chakaraborty, Tushar K., "Stuies towards the development of cyclic peptide–based analogs of macrolide immunosuppressants," Pure Appl. Chem., 1996, 68(3), 565–568.

Ponticelli, Claudio, "Treatment of the Nephrotic Syndrome with Cyclosporin A," J. of Autoimmunity, 1992, 5, 315–24.

Tindall, Richard S.A., "Immunointervention with Cyclosporin A in utoimmune Neurological Disorders," J. of Autoimmunity, 1992, 5, 301–13.

Tugwell, Peter, "Clyclosprin in the Treatment of Rheumatoid Arthritis," J. of Autoimmunity, 1992, 5, 231–40.

Fry, Lionel, "Psoriasis: Immunopathology and Long–term treatment with Cyclosporin," J. of Autoimmunity, 1992, 5, 277–83.

Feutren, Gilles, "The Optimal use of Cyclosporin A in Autoimmune Diseases," J. of Autoimmunity, 1992, 5, 183–95.

Slee, Deborah H. et al., Selectivity in the Inhibition of HIV and FIV Protease: Inhibitory and Mechanistic Studies of Pyrrolidine–Containing α–Keto Amide and Hydroxyethylamine Core Structures, J. Am. Chem. Soc., 1995, 117(48), 1187–78.

Nicolaou, K.C. et al., "Total synthesis of rapamycin," Che.—Eur. J., 1995, 1(5), 318–33.

Munoz, Benito et al., "α–Ketoamide Phe–Pro isostere as a new core structure for the inhibition of HIV protease," Bioorg. Med. Chem., 1994, 2(10), 1085–90.

Hauske, James R. et al., "Investigation of the effects of synthetic, non–cytotoxic immunophilin inhibitors on MDR," Bioorg. Med. Chem.. Lett., 1994, 4(17), 2097–102.

Mashkovskii, M.D. et al., "1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties," Khim.–Farm, Zh., 1993, 27(10), 16–20. (Russian).

Ranganathan, Darshan et al., "Protein Backbone Modification by Novel Cα–C Side–Chain Scission," 1994, J. Am. Chem. Soc., 116(15), 6545–57.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Holt, Dennis A. et al., "Structure–activity of synthetic FKBP ligands as peptidyl–prolyl isomerase inhibitors," Bioorg. Med. Chem. Lett., 1994, 4(2), 315–20.

Karle, Isabella L. et al., "Coformation of the oxalamide group in retro–bispeptides. Three crystal structures," Int. J. Pept. Protein Res., 1994, 43(2), 160–5.

Kaczmar, et al., Makromol. Chem., 1976, 177, 1981–9.

Steiner, Joseph P. et al., "High brain densities of the immunophilin FKBP colocalized with calcineurin," Nature Lett., 1992, 358, 584–7.

Pattenden, Gerald and Tnkard, Mark, "Facile Synthesis of the tricarbonyl subunit in the immunosuppressant rapamycin," Tetrahadron Lett., 1993, 34(16), 2677–80.

Furber, M. et al., "Studies relating to the immunosuppressive activitiy of FK506," Tetrahedron Lett., 1993, 34(8), 1351–4.

Ranganathan, Darshan et al., "Oxalopeptides as core motifs for Protein design," J. Chem. Soc., 1993, (1), 92–4.

Dawson, Ted M. et al., "Imminosuppressant FK506 enhances phosphorylation of nitric oxide synthase and protects against glutamate neurotoxicity," Proc. Natl. Acad. Sci. USA, 1993, 90, 9808–12.

Cunliffe, C. Jane et al., "Novel inhibitors of prolyl 4–hydroxylase. 3. Inhibition by the substrate analog N–oxaloglycine and its derivatives," J. Med. Chem., 1992, 35(14), 2652–8.

Waldmann, Herbert, "Amino acid esters as chiral auxiliaries in Barbier–type reactions in aqueous solutions," Liebigs Ann. Chem., 1991, (12), 1317–22. (German).

Krit, N.A. et al., "Impact of the nature of alkyl radical on the biological activity of N–carboxyalkyl dipeptides," Khim.–Farm. Zh., 1991, 25(7), 44–6. (Russian).

Blaschke et al., Chemical abstracts, 1974, 85, 78505k.

Caufield, Craig E. and Musser, John H., Annual Reports in Medicinal Chemistry, Johns (Ed)., Academic Press, Inc., Chapter 21, 195–204, 1989.

Effenberger F. et al., "Diastereoselective addition of benzenesulfenyl chloride to 1–acryloylproline esters," Chemical Abstracts, 1989, 10, 778–9.

Nakatsuta, M et al. "Total Synthesis of FK506 and an FKBP Reagent, $(C_8, C_9-^{13}C_2)$–FK–506," J. Am. Chem. Soc., 1990, 112 (14), 5583–90.

Shu, A. et al., "Synthesis of I–125 labeled photoaffinity rapamycin analogs," J. Labelled Compd. Radiopharm., 1996, 38(3), 277–37.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cylcosporin hybrid marocycles," Bioorg. Med. Chem. Lett., 1995, 5(20), 2341–6.

Stocks, M. et al., "Macrocyclic ring closures employing the intramolecular Heck reaction," Tetrahedron Lett., 1995, 36(36), 6555–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Armistead, D.M. et al., "Design, synthesis and structure of non–macrocyclic inhibitors of FKBP12, the major binding protin for the immunosupprssant FK506," Acta Crystallogr. 1995, D51(4), 522–8.

Luengo, J. et al., "Structure–activity studies of rapamycin analogs: evidence that the C–7 methodoxy group is part of the effector domain and positioned at the FKBP:12–FRAP interface," Chem. Biol., 1995, 2(7), 471–81.

Furber, Mark, "FKBP–12–ligand–calceineurin interactions: analogs of SBL506," J. Am. Chem. Soc., 1995, 117(27), 7267–8.

Chakraborty, TK et al., "Design and Synthesis of a rapamycin–based high affinity binding FKBP12 ligand," Chem. Biol., 1995, 2(3), 157–61.

Wang, C.P. et al., "A high performance liquid chromatographic method for the determination of rapamycin {sirolimus} in rat serum, plasma, and blood and in monkey serum," J. Liq. Chromatogr., 1995, 18(9), 1801–8.

Smith, A.B. et al., "Total synthesis of rapamycin and demethoxyrapamycin," J. Am. Chem. Soc., 1995, 117(19), 5407–8.

Baumann, K. et al., "Synthesis and oxidative cleavage of the major equilibrium products of ascomycin and Fk 506," Tetrahedron Lett., 1995, 26(13), 2231–4.

Nelson, F. et al., "A novel ring contraction of rapamycin," Tetrahedron Lett., 1994, 35(41), 7557–60.

Dawson, T.M. et al., "The immunophilins, FK506 binding and cyclophilin, are discretely localized in the brain: relationship to calcineurin," Neuroscience, 1994, 62(2), 569–80.

Cameron, Andres et al. "Immunophilin FK506 binding protein associated with inositol 1,4,5–triphosphate receptor modulates calcium flux," Proc. Natl. Acad. Sci. USA, 1995, 92, 1784–1788.

Stocks, M. et al., "The contribution to the binding of the pyranoside sustituents in the excised binding domain of FK–506," Bioorg. Med. Chem. Lett., 1994, 4(12), 1457–60.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Lyons, W. Ernest et al., "Neronal Regeneration Enhances the Expression of the Immunophilin FKBP–12," The Journal of Neuroscience, 1995, 15, 2985–94.

Skotnicki, Jerauld et al., "Ring expanded rapamycin derivatives," Tetrahedron Lett., 1994, 35(2), 201–2.

Skotnicki, Jerauld et al., "Synthesis of secorapamycin estes and amides," Tetrah. Lett., 1994, 35(2), 197–200.

Rao, A.V. Rama and Desibhatla, Vidyanand, "Studies directed towards the syntesis of rapamycin: stereoselective synthesis of C–1 to C–15 segment," Tetrahedron Lett., 1993, 34(44), 7111–14.

Andrus, Merrit B., "Structure–based design of an acyclic ligand that bridges FKBP12 and calcineurin," J. Am. Chem. Soc., 1993, 115(2), 10420–1.

Luengo, Juan I. et al., "Efficient removal of pipecolinate from rapamycin and FK506 by reaction with tetrabutylammonium cyanide," Tetrahedron Lett., 1993, 34(29), 4599–602.

Steffan, Robert J. et al., "Base catalyzed degradations of rapamycin," Tetrahedron Lett., 1993, 34(23), 3699–702.

Nicolaou, K.C. et al., "Total Synthesis of rapamycin," J. Am. Chem. Soc., 1993, 115(10), 4419–20.

Hayward, C.M. et al., "Total Synthesis of rapamycin via a novel titanium–mediated aldol macrocyclization reaction," J. Am. Chem. Soc., 1993, 115(20), 9345–6.

Yohannes, Daniel et al., "Degradation of rapamycin: synthesis of a rapamycin–derived fragment containing the tricarbonyl and triene sectors, " Tetrahedron Lett., 1993, 34(13), 2075–8.

Luengo, J. et al., "Studies on the chemistry of rapamycin: novel transformation under Lewis–acid catalysis," Tetrahedron Lett., 1993, 345(6), 991–4.

Yohannes, Daniel et al., "Degradation of rapamycin: retrieval of major intact subunits," Tetrahedron Lett., 1992, 33(49), 7469–72.

Goulet, Mark T. and Boger, Joshua, "Degradative studies on the tricarbonyl containing macrolide rapamycin," Tetrahedron Lett., 1991, 32(45), 6454.

Goulet, Mark T. et al., "Construction of the FK–506 analog from rapamycin–derived materials," Tetrahedron Lett., 1991, 32(36), 4627–30.

Rao, A.V. Rama et al., "Studies directed towards the synthesis of immunosuppressive agent FK–506: synthesis of the entire bottom half," Tetrahedron Lett., 1991, 32(9), 1251–4.

Fisher, Matthew et al., "On the remarkable propensity for carbon–carbon bond cleavage reactions in teh C(8)–C(10) region of FK–506," J. Org. Chem., 1991, 56(8), 2900–7.

Linde, Robert G. et al., "Straightforward synthesis of 1,2, 3–tricarbonyl systems," J. Org. Chem., 1991, 56(7), 2534–8.

Hayward, C.M. et al., "An application of Suarez reaction to the regiospecific synthesis of the $C_{28}$–$C_{42}$ segment of rapamycin," 3989–92, 1993.

Hovarth, R., et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Ando, Takao et al., "Formation of Crossed Phenzine from the Reaction between Tetra–p–anisyl–and Tetra–p–tolyl–hydrazines in Liquid Sulphur Dioxide," Chem. Comm., S. Chem. Comm., 1975, 989.

Kino, Toru et al., "FK–506, A novel immunosuppressnt isolateded from A Streptomyces," J. of Antibiotics, 1987, 40(9), 1249–55.

Waldmann, Herbert, "Proline benzyl ester as chiral auxilary in Barbier–type reactions in aqueous solution," 1990, Synlett, 10, 627–8.

ROTAMASE ENZYME ACTIVITY INHIBITORS

This application is a continuation-in-part of U.S. patent application Ser. No. 08/551,026, filed Oct. 31, 1995, now abandoned.

BACKGROUND OF THE INVENTION

1. Field of the Invention

This invention relates to the method of using neurotrophic FKBP inhibitor compounds having an affinity for FKBP-type immunophilins as inhibitors of the enzyme activity associated with immunophilin proteins, and particularly inhibitors of peptidyl-prolyl isomerase or rotamase enzyme activity.

2. Description of the Prior Art

The term immunophilin refers to a number of proteins that serve as receptors for the principal immunosuppressant drugs, cyclosporin A (CsA), FK506, and rapamycin. Known classes of immunophilins are cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Instead immunosuppression appears to stem from the formation of a complex of immunosuppressant drugs and immunophilins. It has been shown that the immunophilin-drug complexes interact with ternary protein targets as their mode of action. In the case of FKBP-FKSO6 and FKBP-CsA, the drug-immunophilin complexes bind to the enzyme calcineurin, inhibiting T-cell receptor signalling leading to T-cell proliferation. Similarly, the complex of rapamycin and FKBP interacts with the RAFT1/FRAP protein and inhibits signalling from the IL-2 receptor.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release, and neuronal process extension.

FK506 also augments the phosphorylation of growth-associated protein-43 (GAP43). GAP43 is involved in neuronal process extension and its phosphorylation appears to augment this activity. Accordingly, the effects of FK506 rapamycin and cyclosporin in neuronal process extension have been examined using PC12 cells. PC12 cells are a continuous line of neuronal-like cells which extend neurites when stimulated by nerve growth factor (NGF).

Surprisingly, it has been found that picomolar concentrations of an immunosuppressant such as FK506 and rapamycin stimulate neurite out growth in PC12 cells and sensory neurons, namely dorsal root ganglion cells (DRGs). In whole animal experiments, FK506 has been shown to stimulate nerve regeneration following facial nerve injury and results in functional recovery in animals with sciatic nerve lesions.

More particularly, it has been found that drugs with a high affinity for FKBP are potent rotamase inhibitors and exhibit excellent neurotrophic effects. Snyder et al., "Immunophilins and the Nervous System", *Nature Medicine*, Volume 1, No. 1, January 1995, 32–37. These findings suggest the use of immunosuppressants in treating various peripheral neuropathies and enhancing neuronal regrowth in the central nervous system (CNS). Studies have demonstrated that neurodegenerative disorders such as Alzheimer's disease and Parkinson's disease may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins such as brain derived growth factor, glial derived growth factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321:1725).

The present invention provides non-immunosuppressive FKBP inhibitor compounds containing is small molecule FKBP rotamase inhibitors which are extremely potent in augmenting neurite outgrowth, and for promoting neuronal growth, and regeneration in various neuropathological situations where neuronal repair can be facilitated including peripheral nerve damage by physical injury or disease state such as diabetes, physical damage to the central nervous system (spinal cord and brain), brain damage associated with stroke, and for the treatment of neurological disorders relating to neurodegeneration, including Parkinson's disease and Alzheimer's disease.

SUMMARY OF THE INVENTION

This invention relates to the method of using neurotrophic FKBP inhibitor compounds having an affinity for FKBP-type immunophilins as inhibitors of the enzyme activity associated with immunophilin proteins, and particularly inhibitors of peptidyl-prolyl isomerase or rotamase enzyme activity.

A preferred embodiment of this invention is a method of treating a neurological activity in an animal, comprising: administering to an animal an effective amount of a FKBP inhibitor having an affinity for FKBP-type immunophilins to stimulate growth of damaged peripheral nerves or to promote neuronal regeneration, wherein the FKBP-type immunophilin exhibits rotamase activity and the pipecolic acid derivative inhibits said rotamase activity of the immunophilin.

Another preferred embodiment of this invention is a method of treating a neurological disorder in an animal, comprising: administering to an animal an effective amount of a FKBP inhibitor having an affinity for FKBP-type immunophilins in combination with an effective amount of a neurotrophic factor selected from the group consisting of neurotrophic growth factor, brain derived growth factor, glial derived growth factor, cilial neurotrophic factor, and neurotropin-3, to stimulate growth of damaged peripheral nerves or to promote neuronal regeneration, wherein the FKBP-type immunophilin exhibits rotamase activity and the pipecolic acid derivative inhibits said rotamase activity of the immunophilin.

Another preferred embodiment of this invention is a method of stimulating growth of damaged peripheral nerves, comprising: administering to damaged peripheral nerves an effective amount of an FKBP inhibitor compound having an affinity for FKBP-type immunophilins to stimulate or promote growth of the damaged peripheral nerves, wherein the FKBP-type immunophilins exhibit rotamase activity and the pipecolic acid derivative inhibits said rotamase activity of the immunophilin.

Another preferred embodiment of this invention is a method of stimulating growth of damaged peripheral nerves, comprising: administering to damaged peripheral nerves an effective amount of an FKBP inhibitor compound having an affinity for FKBP-type immunophilins to stimulate growth of damaged peripheral nerves, wherein the FKBP-type immunophilin exhibit rotamase activity and the pipecolic acid derivative inhibits said rotamase activity of the immunophilin.

Another preferred embodiment of this invention is a method for promoting neuronal regeneration and growth in animals, comprising: administering to an animal an effective amount of an FKBP inhibitor compound having an affinity for FKBP-type immunophilins to promote neuronal regeneration, wherein the FKBP-type immunophilins exhibit rotamase activity and the pipecolic acid derivative inhibits said rotamase activity of the immunophilin. Yet another preferred embodiment of this invention is a method for preventing neurodegeneration in an animal, comprising: administering to an animal an effective amount of an FKBP inhibitor having an affinity for FKBP-type immunophilins to prevent neurodegeneration, wherein the FKBP-type immunophilin exhibits rotamase activity and the pipecolic acid derivative inhibits said rotamase activity of the immunophilin.

BRIEF DESCRIPTION OF THE DRAWINGS

FIG. 1 shows the data from 6–10 different concentrations used to generate typical dose-response curves, from which $ED_{50}$ values were calculated.

FIG. 2 shows the data from 6–10 different concentrations used to generate typical dose-response curves, from which $ED_{50}$ values were calculated.

FIG. 3 shows the dose-response for Example 21 in cultured sensory neurons.

FIG. 4 shows the effect of 300 pM of Example 15 on neurite outgrowth in cultured sensory neurons.

FIG. 5 shows the effect of 1 nM of Example 22 on neurite outgrowth in cultured sensory neurons.

DETAILED DESCRIPTION OF THE INVENTION

The novel neurotrophic FKBP inhibitor compounds of this invention have an affinity for the FK506 binding proteins such as FKBP-12. When the neurotrophic compounds of the invention are bound to FKBP, they have been found to inhibit the prolyl-peptidyl cis-trans isomerase activity, or rotamase activity of the binding protein and unexpectedly stimulate neurite growth.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; aralkyl halides like benzyl and phenethyl bromides; and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, porphyria, or Gullain-Barré syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the immunophilin-drug complex should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

METHODS AND PROCEDURES

Figure 5:
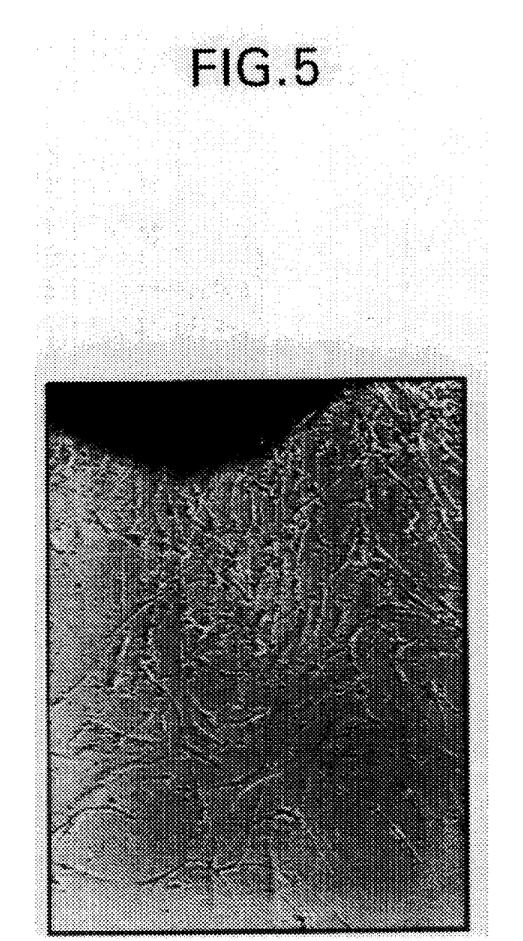
FIG. 5 is a representative photomicrograph of a sensory neuron responding to trophic effects of the drugs.

Nerve Extension Elicited in Chick Dorsal Root Ganglia by Non-Immunosuppressive Ligands of Immunophilins In previous studies, it has been observed that neurotrophic effects of immunosuppressant drugs in explants of rat dorsal root ganglia with significant augmentation in nerve outgrowth has occurred with FK506 concentrations as low as 1 picomolar (Lyons et. al., 1994). In the rat ganglia neurotrophic effects were observed with FK506 even in the absence of NGF. In the present work explants of chick dorsal root ganglia have been used, which are easier to employ in studies of nerve outgrowth. In the absence of added NGF, we have observed minimal effects of immunophilin ligand drugs. The chick cells are more sensitive to NGF than PC-12 cells so that we employ 0.1 ng/ml NGF to produce minimal neurite outgrowth and to demonstrate neurotrophic actions of immunophilin ligands (FIG. 5).

The maximal increase in the number of processes, their length and branching is quite similar at maximally effective contractions of the immunophilin ligands and of NGF (100 ng/ml). With progressively increasing concentrations of the various drugs, one observes a larger number of processes, more extensive branching and a greater length of individual processes.

We evaluated the potencies of drugs in binding to FKBP-12 by examining inhibition of peptidyl prolyl-isomerase activity and inhibition of ³H-FK506 binding to recombinant FKBP-12 (Table 1). There is a striking parallel between their potencies in stimulating neurite outgrowth and inhibiting rotamase activity.

The very close correlation between the potencies of drugs in binding to immunophilins, inhibiting their rotamase activity and stimulating neurite outgrowth implies that inhibition of rotamase activity is responsible for neurotrophic effects of the drugs. The extraordinarily high potency of the drugs in stimulating neurite outgrowth and in binding to immunophilins makes it most unlikely that any other target could account for the neurotrophic effects.

Because of the extraordinary potency of the drugs and the close correlation between rotamase inhibition and neurotrophic actions, we conclude that rotamase inhibition is likely involved in neurotrophic effects. A number of proteins have been reported as substrates for the rotamase activity of immunophilins including collagen (Steinmann et. al., 1991) and transferring (Lodish and King, 1991). Recently highly purified preparations of ryanodine receptor and the IP-3 receptor, prominent intracellular calcium channels, have been reported to exist in a complex with FKBP-12. Dissociation of FKBP-12 from these complexes causes the calcium channels to become "leaky" (Cameron et. al., 1995). Calcium fluxes are involved in neurite extension so that the IP-3 receptor and the ryanodine receptor might be involved in the neurotrophic effects of drugs. Since the drugs bind to the same site on FKBP-12 as the IP-3 receptor or the ryanodine receptor, one would have to postulate that the drugs displace the channels from FKBP-12. No interaction between these calcium channels in cyclophilin has been reported so that this model would not explain the neurotrophic actions of cyclosporin A.

The neurotrophic actions of the drugs studied here are exerted at extremely low concentrations indicating potencies comparable to those of neurotrophic proteins such as brain derived growth factor, neurotropin-3 and neurotrophic growth factor.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

Illustrative generic FKBP inhibitor compounds which can be used for the purposes of this invention include:

and pharmaceutically acceptable salts thereof, wherein A is $CH_2$, O, NH, or N-($C_1$-$C_4$ alkyl);

wherein B and D are independently Ar, (C5–C7)-cycloalkyl substituted (C1–C6)-straight or branched alkyl or alkenyl, (C5–C7)-cycloalkenyl substituted (C1–C6)-straight or branched alkyl or alkenyl, or Ar substituted (C1–C6)-straight or branched alkyl or alkenyl, wherein in each case, one or two carbon atoms of the straight or branched alkyl or alkenyl groups may be substituted with 1–2 heteroatoms selected from the group consisting of oxygen, sulfur, SO and $SO_2$ in chemically reasonable substitution patterns, or wherein Q is hydrogen, (C1–C6)-straight or branched alkyl or (C1–C6)-straight or branched alkenyl;

wherein T is Ar or substituted 5–7 membered cycloalkyl with substituents at positions 3 and 4 which are independently selected from the group consisting of hydrogen, hydroxyl, O-(C1–C4)-alkyl or O-(C1–C4)-alkenyl and carbonyl;

wherein Ar is selected from the group consisting of 1-napthyl, 2-napthyl, 2-furyl, 3-furyl, 2-thienyl, 3-thienyl, 2-pyridyl, 3-pyridyl, 4-pyridyl and phenyl, monocyclic and bicyclic heterocyclic ring systems with individual ring sizes being 5 or 6 which may contain in either or both rings a total of 1–4 heteroatoms independently selected from oxygen, nitrogen and sulfur; wherein Ar may contain one to three substituents which are independently selected from the group consisting of hydrogen, halo, hydroxyl, hydroxymethyl, nitro, CF3, trifluoromethoxy, (C1–C6)-straight or branched alkyl or (C1–C6)-straight or branched alkenyl, O-(C1–C4)-straight or branched alkyl or O-(C1–C4)-straight or branched alkenyl, O-benzyl, O-phenyl, amino, 1,2-methylenedioxy, carbonyl and phenyl;

wherein L is either hydrogen or U; M is either oxygen or CH—U, provided that if L is hydrogen, then M is CH—U, or if M is oxygen then L is U;

wherein U is hydrogen, O-(C1–C4)-straight or branched alkyl or O-(C1–C4)-straight or branched alkenyl, (C1–C6)-straight or branched alkyl or (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C1–C4)-alkyl or (C1–C4)-alkenyl]-Ar or Ar (Ar as described above);

wherein J is hydrogen or C1 or C2 alkyl or benzyl; K is (C1–C4)-straight or branched alkyl, benzyl or cyclohexylethyl; or wherein J and K may be taken together to form a 5–7 membered heterocyclic ring which may contain an oxygen (O), sulfur (S), SO or $SO_2$ substituted therein; and wherein n is 0–3.

The stereochemistry at position 1 (Formula I) is (R) or (S), with (S) preferred. The stereochemistry at position 2 is (R) or (S).

Illustrative preferred FKBP inhibitor compounds which can be used for the purposes of this invention are described in U.S. Pat. No. 5,330,993, the contents of which is incorporated herein by reference. Exemplary compounds include those having the formula:

and pharmaceutically acceptable salts thereof,
wherein A is O, NH, or N-(C1–C4 alkyl);
wherein B is hydrogen, CHL—Ar, (C1–C6)-straight or branched alkyl, (C1–C6)-straight or branched alkenyl, (C5–C7)-cycloalkyl, (C5–C7)-cycloalkenyl or Ar substituted (C1–C6)-alkyl or alkenyl, or wherein L and Q are independently hydrogen, (C114 C6)-straight or branched alkyl or (C1–C6)-straight or branched alkenyl;
wherein T is Ar or substituted cyclohexyl with substituents at positions 3 and 4 which are independently selected from the group consisting of hydrogen, hydroxyl, O-(C1–C4)-alkyl or O-(C1–C4)-alkenyl and carbonyl;
wherein Ar is selected from the group consisting of 1-napthyl, 2-napthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, CF3, (C1–C6)-straight or branched alkyl or (C1–C6-straight or branched alkenyl, O-(C1–C4)-straight or branched alkyl or O-(C1–C4)-straight or branched alkenyl, O-benzyl, O-phenyl, amino and phenyl;
wherein D is either hydrogen or U; E is either oxygen or CH—U, provided that if D is hydrogen, then E is CH—U, or if E is oxygen then D is U;
wherein U is hydrogen, O-(C1–C4)-straight or branched alkyl or O-(C1–C4)-straight or branched alkenyl, (C1–C6)-straight or branched alkyl or (C1–C6)-straight or branched alkenyl,(C5–C7)-cycloalkyl, (C5–C7)-cycloalkenyl substituted with (C1–C4)-straight or branched alkyl or (C1–C4)-straight or branched alkenyl, 2-indolyl, 3-indolyl, [(C1–C4)-alkyl or (C1–C4)-alkenyl]-Ar or Ar (Ar as described above);
wherein J is hydrogen or C1 or C2 alkyl or benzyl; K is (C1–C4)-straight or branched alkyl, benzyl or cyclohexylethyl; or wherein J and K may be taken together to form a 5–7 membered heterocyclic ring which may contain an oxygen (O), sulfur (S), SO or SO2 substituted therein.

The stereochemistry at position 1 (Formula I) is (R) or (S), with (S) preferred.

$K_1$ Test Procedure

Inhibition of the peptidyl-prolyl isomerase (rotamase) activity of the compounds used herein can be evaluated by known methods described in the literature (Harding, M. W. et al. *Nature* 341:758–760 (1989); Holt et al. *J. Am. Chem. Soc.* 115:9923–9938). These values are obtained as apparent $\kappa$'s and are presented for various compounds in Table I. The cis-trans isomerization of an alanine-proline bond in a model substrate, N-succinyl-Ala-Ala-Pro-Phe-p-nitroanilide, is monitored spectrophotometrically in a chymotrypsin-coupled assay, well known to those skilled in the art, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $\kappa$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 sec using a spectrophotometer and the rate constants are determined from the absorbance versus time data files.

The data for these experiments is presented in Tables I and IV.

TABLE I

| No. | B | D | n | K |
|---|---|---|---|---|
| 1 | Benzyl | Phenyl | 2 | 1.5 µM |
| 2 | 3-Phenylpropyl | Phenyl | 2 | |
| 3 | 4-(4-Methoxy-phenyl) butyl | Phenyl | 2 | |
| 4 | 4-Phenylbutyl | Phenyl | 2 | 0.35 µM |
| 5 | Phenethyl | Phenyl | 2 | 1.1 µM |
| 6 | 4-Cyclohexyl-butyl | Phenyl | 2 | 0.4 µM |
| 7 | Benzyl | Methoxy | 2 | 80 µM |
| 8 | 4-Cyclohexyl-butyl | Methoxy | 2 | 6 µM |
| 9 | 3-Cyclohexyl-propyl | Methoxy | 2 | 20 µM |
| 10 | 3-Cyclopentyl-propyl | Methoxy | 2 | 35 µM |
| 11 | Benzyl | 2-Furyl | 2 | 3 µM |
| 12 | 4-Cyclohexyl-butyl | 3,4,5-Trimethoxy-phenyl | 2 | 0.04 µM |
| 13 | 3-Phenoxy-benzyl | 3,4,5-Trimethoxy-phenyl | 2 | 0.018 µM |
| 14 | 4-Phenylbutyl | 3,4,5-Trimethoxy-phenyl | 2 | 0.019 µM |
| 15 | 3-(3-Indolyl)propyl | 3,4,5-Trimethoxy-phenyl | 2 | 0.017 µM |
| 16 | 4-(4-Methoxy-phenyl) butyl | 3,4,5-Trimethoxy-phenyl | 2 | 0.013 µM |

TABLE II

| No. | n | m | B | D | L |
|---|---|---|---|---|---|
| 17 | 2 | 0 | 3-Phenylpropyl | 3-(3-Pyridyl)propyl | Phenyl |
| 18 | 2 | 0 | 3-Phenylpropyl | 3-(2-Pyridyl)propyl | Phenyl |
| 19 | 2 | 0 | 3-Phenylpropyl | 2-(4-Methoxyphenyl)ethyl | Phenyl |
| 20 | 2 | 0 | 3-Phenylpropyl | 3-Phenylpropyl | Phenyl |
| 21 | 2 | 0 | 3-Phenylpropyl | 3-Phenylpropyl | 3,4,5-Trimethoxyphenyl |
| 22 | 2 | 0 | 3-Phenylpropyl | 2-(3-Pyridyl) | 3,4,5-Trimethoxyphenyl |
| 23 | 2 | 0 | 3-Phenylpropyl | 3-(2-Pyridyl) | 3,4,5-Trimethoxyphenyl |
| 24 | 2 | 0 | 3-Phenylpropyl | 3-(4-Methoxyphenyl) propyl | 3,4,5-Trimethoxyphenyl |
| 25 | 2 | 0 | 3-Phenylpropyl | 3-(3-Pyridyl)propoxy- | 3-Isopropyl phenyl |

Chick Dorsal Root Ganglion Cultures and Neurite Outgrowth

Figure 1:
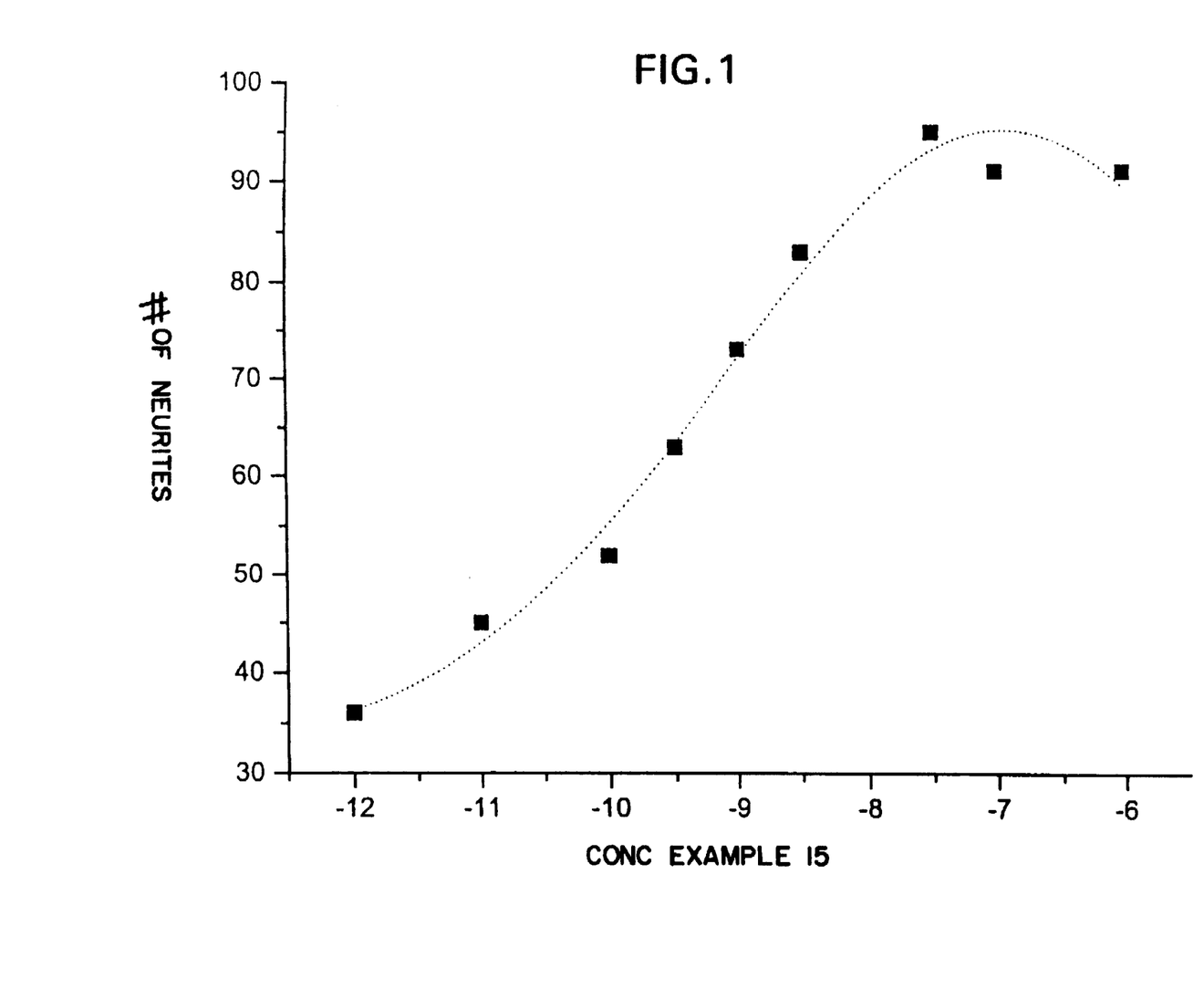
FIG. 1 is a dose-response curve for Example 15.
Figure 2:
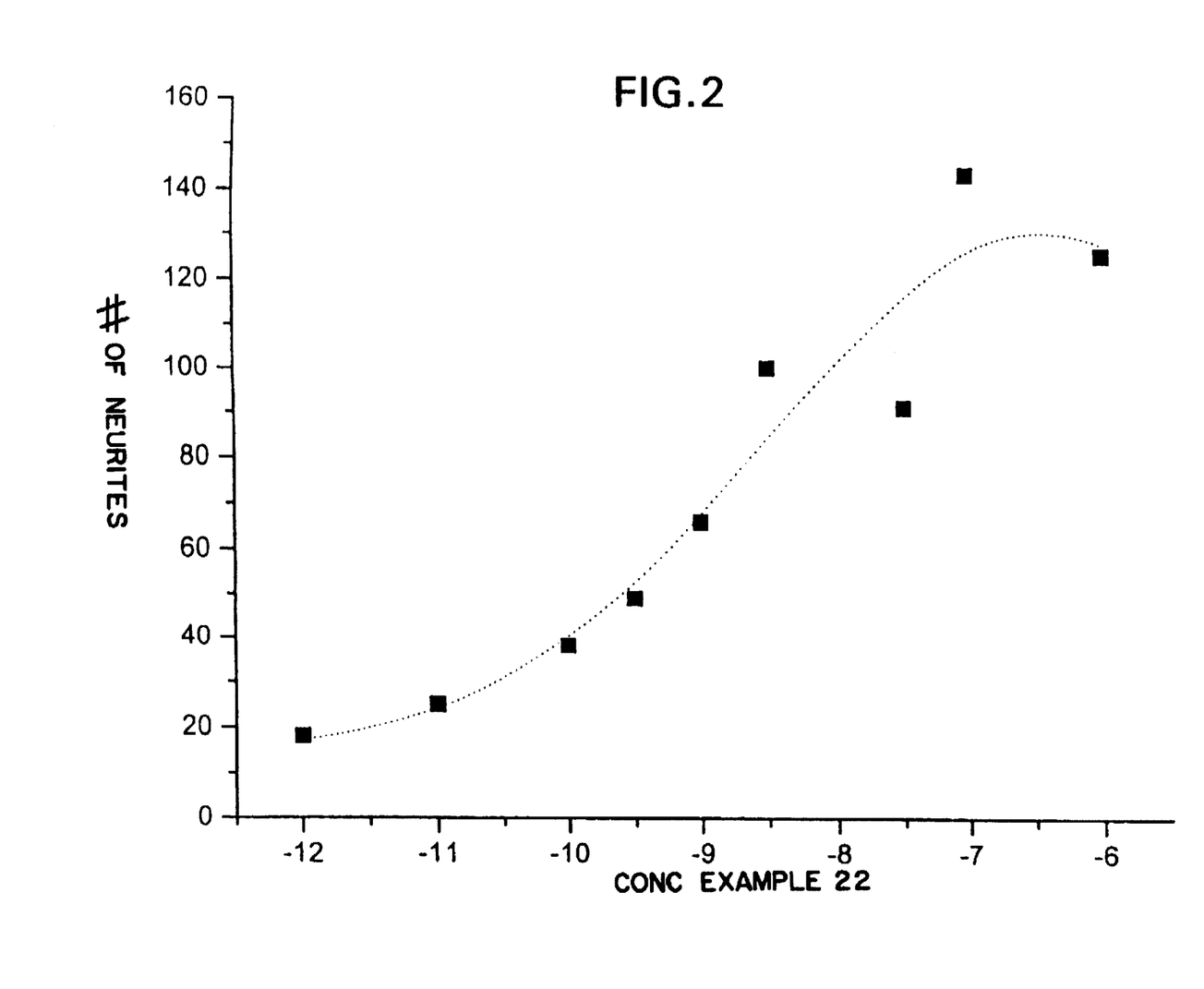
FIG. 2 is a dose-response curve for Example 22.

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 µM cytosine β-D arabinofuranoside (Ara C) at 37° C. in an environment containing 5% $CO_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate. Data from 6–10 different concentrations were used to generate dose-response curves, from which $ED_{50}$ values were calculated. Typical response curves are shown in FIGS. 1 and 2 for examples 15 and 22, respectively.

Figure 3A:
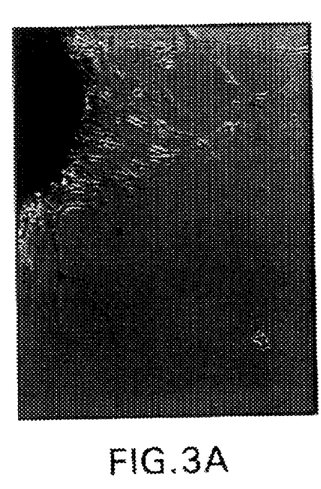
FIG. 3 is a representative photomicrograph of a sensory neuron responding to trophic effects of the drugs.
Figure 3B:
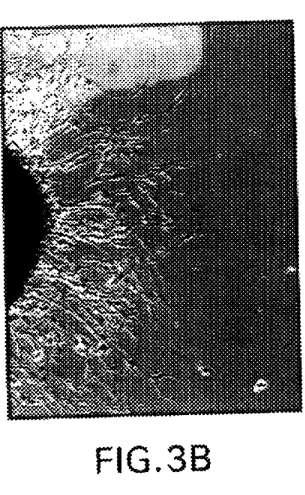
Figure 3C:
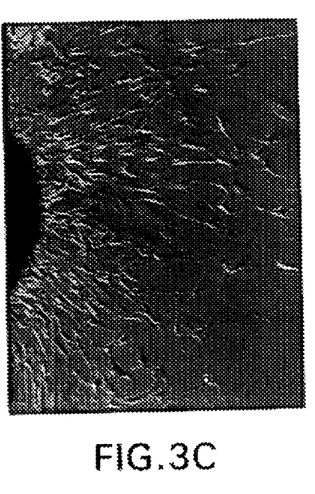
Figure 4:
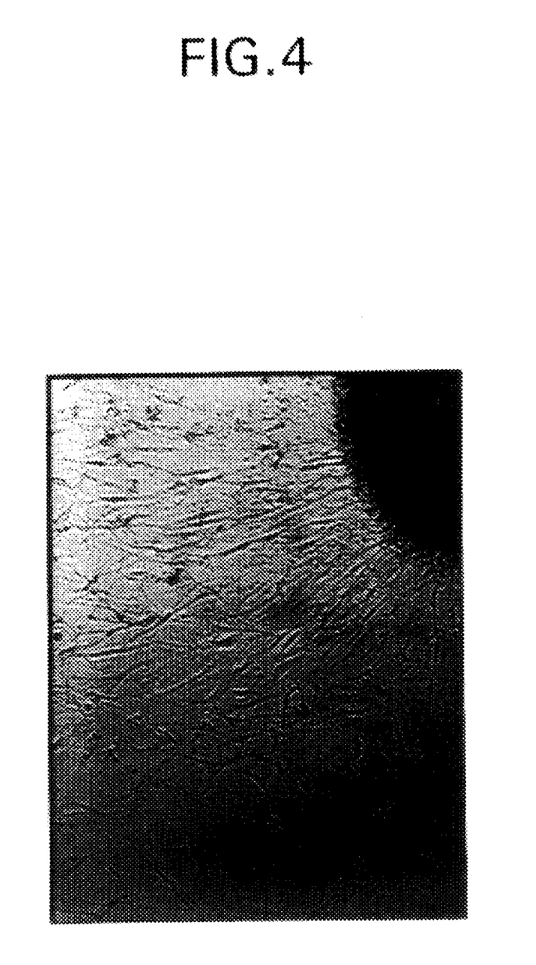
FIG. 4 is a representative photomicrograph of a sensory neuron responding to trophic effects of the drugs.

Data for these experiments are presented in Tables III and IV. Representative photomicrographs of sensory neurons responding to the trophic effects of the drugs are shown in FIGS. 3–5. FIG. 3 demonstrates the dose-dependent neurotrophic effects of example 21 on neuronal cultures. FIG. 4 demonstrates the stimulation of neurite outgrowth induced by a 300 pM dose of example 15 and, FIG. 5 demonstrates the stimulation of neurite outgrowth induced by a 1 nM dose of example 22.

TABLE III

Neurite Outgrowth in Chick DRG

| Example | $ED_{50}$, nM Neurite Outgrowth in DRG cultures |
|---|---|
| 1 | 25–100 |
| 2 | 10–20 |
| 3 | 0.500 |
| 4 | 25–100 |
| 5 | 25–100 |
| 6 | 10–20 |
| 7 | >10,000 |
| 8 | >10,000 |
| 9 | >10,000 |
| 10 | >10,000 |
| 11 | 1000 |
| 12 | 0.031 |
| 13 | 0.180 |
| 14 | 1–5 |
| 15 | 0.055 |
| 16 | 0.030 |

TABLE IV

Biological Results

| Compound | K, nM | $ED_{50}$, nM Neurite Outgrowth in DRG cultures |
|---|---|---|
| 17 | 56 | 1–5 |
| 18 | 50 | 0.063 |
| 19 | 270 | 10–20 |
| 20 | — | 0.0044 |
| 21 | 1.0 | 0.61 |
| 22 | 3.0 | 0.95 |
| 23 | 1.0 | 25 |
| 24 | 3.0 | 0.50 |
| 25 | 2.0 | 0.30 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of stimulating growth of damaged nerves in an animal which damage is not caused by amyotrophic lateral sclerosis, comprising:

administering to said animal an effective non-immunosuppressive amount of a pipecolic acid derivative consisting essentially of a compound represented by the formula:

or a pharmaceutically acceptable salt thereof, wherein A is O, NH, or N-(C1–C4 alkyl);

wherein B is hydrogen, CHL—Ar, (C1–C6)-straight or branched alkyl, (C1–C6)-straight or branched alkenyl, (C5–C7)-cycloalkyl, (C5–C7)-cycloalkenyl or Ar substituted (C1–C6)-alkyl or alkenyl, or wherein L and Q are independently hydrogen, (C1–C6)-straight or branched alkyl or (C1–C6)-straight or branched alkenyl;

wherein T is Ar or substituted cyclohexyl with substituents at positions 3 and 4 which are independently selected from the group consisting of hydrogen, hydroxyl, O-(C1–C4)-alkyl or O-(C1–C4)-alkenyl and carbonyl;

wherein Ar is selected from the group consisting of 1-napthyl, 2-napthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, CF3, (C1–C6)-straight or branched alkyl or (C1–C6)-straight or branched alkenyl, O-(C1–C4)-straight or branched alkyl or O-(C1–C4)-straight or branched alkenyl, O-benzyl, O-phenyl, amino and phenyl.

wherein D is either hydrogen or U; E is either oxygen or CH—U, provided that if D is hydrogen, then E is CH—U, or if E is oxygen then D is U;

wherein U is hydrogen, O-(C1–C4)-straight or branched alkyl or O-(C1–C4)-straight or branched alkenyl, (C1–C6)-straight or branched alkyl or (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, 2-indolyl, 3-indolyl, [(C1–C4)-alkyl or (C1–C4)-alkenyl]-Ar or Ar (Ar as described above);

wherein J is hydrogen or C1 or C2 alkyl or benzyl; K is (C1–C4)-straight or branched alkyl, benzyl or cyclohexylethyl; or wherein J and K may be taken together to form a 5–7 membered heterocyclic ring which may contain an oxygen (O), sulfur (S), SO or SO2 substituted therein.

2. A method of stimulating growth of damaged peripheral nerves in an animal, which damage is not caused by amyotrophic lateral sclerosis, comprising:

administering to said animal an effective non-immunosuppressive amount of a pipecolic acid derivative compound according to claim 1.

3. A method of stimulating growth of damaged nerves in an animal which damage is not caused by amyotrophic lateral sclerosis, comprising:

administering to said animal an effective non-immunosuppressive amount of a pipecolic acid derivative consisting essentially of a compound represented by the formula:

wherein:

when n is 2, D is phenyl, and B is benzyl, 3-phenylpropyl, 4-(4-methoxyphenyl)butyl, 4-phenylbutyl, phenethyl, or 4-cyclohexylbutyl;

when n is 2, D is methoxy, and B is benzyl, 4-cyclohexylbutyl, 3-cyclohexylpropyl, or 3-cyclopenylpropyl;

when n is 2, D is 2-furyl, and B is benzyl; and when n is 2, D is 3,4,5-trimethoxyphenyl, and B is 4-cyclohexylbutyl, 3-phenoxybenzyl, 4-phenylbutyl, 3-(3-indolyl)propyl, or 4-(4-methoxyphenyl)butyl.

4. A method of stimulating growth of damaged peripheral nerves in an animal which damage is not caused by amyotrophic lateral sclerosis, comprising:

administering to said animal an effective non-immunosuppressive amount of a pipecolic acid derivative according to claim 3.

* * * * *